United States Patent
Kobayashi

(10) Patent No.: US 10,641,908 B2
(45) Date of Patent: May 5, 2020

(54) RADIATION IMAGING APPARATUS, RADIATION IMAGING METHOD, AND COMPUTER READABLE STORAGE MEDIUM

(71) Applicant: CANON KABUSHIKI KAISHA, Tokyo (JP)

(72) Inventor: Tsuyoshi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 135 days.

(21) Appl. No.: 15/987,078

(22) Filed: May 23, 2018

(65) Prior Publication Data

US 2018/0348378 A1    Dec. 6, 2018

(30) Foreign Application Priority Data

May 31, 2017  (JP) ................. 2017-108322

(51) Int. Cl.
| | | |
|---|---|---|
| *G01T 1/24* | (2006.01) | |
| *G01T 1/16* | (2006.01) | |
| *G01T 1/17* | (2006.01) | |
| *G01T 7/00* | (2006.01) | |
| *A61B 6/00* | (2006.01) | |

(52) U.S. Cl.
CPC .......... *G01T 1/1606* (2013.01); *A61B 6/4208* (2013.01); *A61B 6/4291* (2013.01); *G01T 1/17* (2013.01); *G01T 7/00* (2013.01)

(58) Field of Classification Search
CPC .......... G02T 1/1606; G01T 1/17; G01T 7/00; A61B 6/4208; A61B 6/4291; A61B 6/40; A61B 6/44; A61B 6/54
See application file for complete search history.

(56) References Cited

U.S. PATENT DOCUMENTS

| | | | |
|---|---|---|---|
| 8,983,035 B2 * | 3/2015 | Noma | H05G 1/64 |
| | | | 250/214 DC |
| 9,025,055 B2 | 5/2015 | Kobayashi | |
| 9,299,141 B2 * | 3/2016 | Takahashi | G06T 7/0012 |
| 2002/0080921 A1 * | 6/2002 | Smith | A61B 6/0457 |
| | | | 378/189 |
| 2013/0223712 A1 | 8/2013 | Kobayashi | |
| 2015/0363918 A1 | 12/2015 | Kobayashi | |

FOREIGN PATENT DOCUMENTS

| | | |
|---|---|---|
| JP | 2014138654 A * | 7/2014 |
| JP | 2016-198469 | 12/2016 |

* cited by examiner

*Primary Examiner* — Kiho Kim
(74) *Attorney, Agent, or Firm* — Venable LLP

(57) ABSTRACT

A radiation imaging apparatus that has a detection unit that detects radiation and outputs image data determines whether or not a grid for scattered ray reduction is installed on the detection unit, and changes a radiation detection range of the detection unit based on the determination result.

19 Claims, 6 Drawing Sheets

| INTEGRATION CAPACITANCE [pF] | 1.5 | 2 | 2.5 | 3 | 3.5 | 4 |
|---|---|---|---|---|---|---|
| SENSITIVITY [count/μGy] | 1600 | 1200 | 960 | 800 | 686 | 600 |
| SATURATION DOSE [μGy] | 40 | 55 | 70 | 80 | 100 | 110 |

REFERENCE SETTING: 2; TARGET: 3

RELATIONSHIP BETWEEN INTEGRATION CAPACITANCE AND SENSITIVITY

RADIATION IMAGING APPARATUS, RADIATION IMAGING METHOD, AND COMPUTER READABLE STORAGE MEDIUM

BACKGROUND OF THE INVENTION

Field of the Invention

The present invention is related to a radiation imaging apparatus, a radiation imaging method, and a computer readable storage medium storing a program for obtaining an image by using radiation.

Description of the Related Art

In recent years, digital radiation imaging apparatuses have become widespread at medical sites. In a detection unit of a digital radiation imaging apparatus, an intensity (dose) of radiation that passes through an object is converted into an electrical signal, the electrical signal is further converted into a digital value, and thereby a radiation image is obtained. In the radiation image, in addition to a signal component corresponding to primary radiation that passes directly from the radiation source through the object, a signal component corresponding to scattered rays that are generated by radiation within the object scattering is included. The signal component corresponding to scattered rays is the cause of deterioration of the contrast in an object image configured by the primary radiation in the radiation image.

In order to avoid object image contrast deterioration due to scattered rays, an anti-scattering grid (hereinafter simply referred to as a grid) is arranged between the object and the detection unit. By this, it is possible to attenuate scattered rays before they reach the detection unit. As a result, the ratio of the signal component of the primary radiation in the radiation that reaches the detection unit increases, and the contrast of the radiation image can be improved. However, using a grid when imaging is an operational burden on the user. This is because there are cases in which a grid is unnecessary depending on the imaging part, and the user must attach/detach the grid in accordance with the imaging part. In Japanese Patent Laid-Open No. 2016-198469 (hereinafter, D1), a technique in which, by using image processing, a component corresponding to scattered rays is estimated in an image imaged without using a grid, that component is removed, and by reducing the scattered ray signal, the contrast of an object image is improved (hereinafter, referred to as scattered ray reduction processing) is proposed.

As in D1, in the method of performing imaging without using a grid and reducing a scattered ray signal by image processing, the primary radiation and scattered rays are both inputted into the detection unit. For that reason, a portion of the dynamic range of the detection unit is occupied by the scattered ray signal. In radiation imaging, irrespective of whether or not there is a grid, the dose of primary radiation does not change much. Because a valid signal for obtaining object information is obtained by the primary radiation, in a case where a grid is not used, it is necessary to irradiate the object with a dose of primary radiation equivalent to when a grid is used in order to obtain an image quality equivalent to when a grid is used.

As a result, the incident dose on the detection unit in the case where a grid is not used increases approximately proportionally to the scattered rays as compared to the case where a grid is used. Furthermore, there are cases in which the dose of scattered rays is not something that is small compared to the dose of primary radiation, and depending on the object, the dose of scattered rays may be greater than or equal to the dose of primary radiation. Accordingly, when imaging is performed without using a grid, the input signal ends up exceeding a maximum value of the detection range of the detection unit, signal saturation occurs, and accurate output cannot be obtained in a portion of the image.

SUMMARY OF THE INVENTION

An embodiment of the present invention was conceived in view of the above problem, and provides a radiation imaging apparatus, a radiation imaging method, and a program by which it is possible to prevent the occurrence of saturation in a detection unit even when imaging is performed without using a grid.

According to one aspect of the present invention, there is provided a radiation imaging apparatus, comprising: a detection unit configured to detect radiation and output image data; a determination unit configured to determine whether or not a grid for scattered ray reduction is installed on the detection unit; and a change unit configured to, based on a determination result of the determination unit, change a radiation detection range of the detection unit.

According to another aspect of the present invention, there is provided a radiation imaging apparatus, comprising: a detection unit configured to detect radiation and output image data according to the detected radiation; a determination unit configured to determine whether or not to execute scattered ray reduction processing for the image data; and a change unit configured to, based on whether or not to execute the scattered ray reduction processing, change a radiation detection range of the detection unit.

According to another aspect of the present invention, there is provided a radiation imaging method for detecting radiation and outputting image data according to the detected radiation, the method comprising: determining whether or not a grid for scattered ray reduction is installed; and changing a radiation detection range based on a result of the determination.

According to another aspect of the present invention, there is provided a radiation imaging method for detecting radiation and outputting image data according to the detected radiation, the method comprising: determining whether or not to execute scattered ray reduction processing for the image data; and based on whether or not to execute the scattered ray reduction processing, changing a radiation detection range.

According to another aspect of the present invention, there is provided a storage medium storing a program for causing a computer to execute a radiation imaging method for detecting radiation and outputting image data according to the detected radiation, the method comprising: determining whether or not a grid for scattered ray reduction is installed; and changing a radiation detection range based on a result of the determination.

According to another aspect of the present invention, there is provided a storage medium storing a program for causing a computer to execute a radiation imaging method for detecting radiation and outputting image data according to the detected radiation, the method comprising: determining whether or not to execute scattered ray reduction processing for the image data; and based on whether or not to execute the scattered ray reduction processing, changing a radiation detection range.

Further features of the present invention will become apparent from the following description of exemplary embodiments (with reference to the attached drawings).

DESCRIPTION OF THE EMBODIMENTS

Hereinafter, explanation will be given regarding a preferred embodiment of the present invention with reference to the attached drawings.

Figure 1:
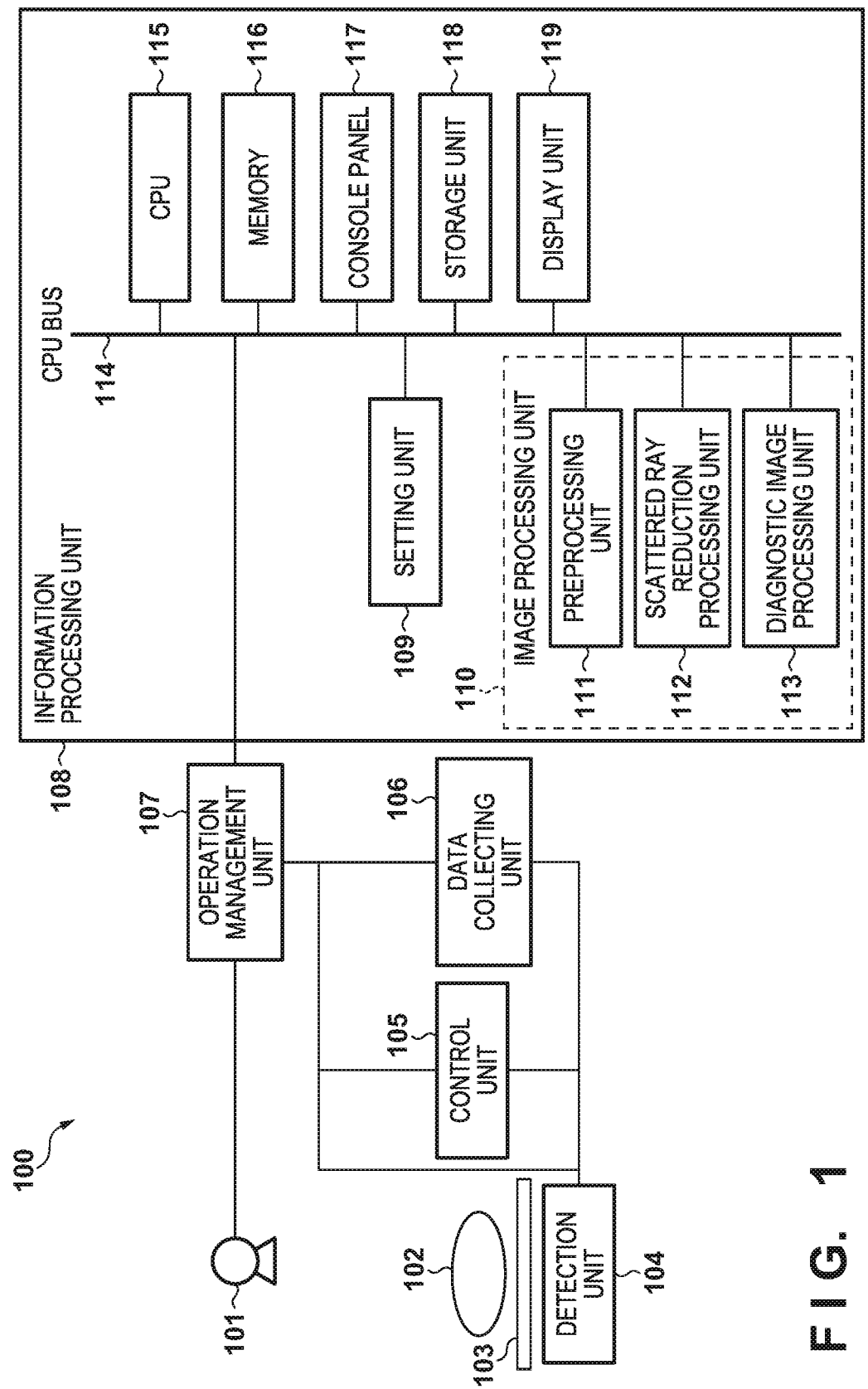
FIG. 1 is a block diagram that illustrates a basic configuration example of a radiation imaging apparatus according to an embodiment.

Firstly, description regarding a configuration example of a radiation imaging apparatus according the embodiment is given using FIG. 1. FIG. 1 is a block diagram that illustrates a basic configuration example of a radiation imaging apparatus according to an embodiment.

In a radiation imaging apparatus 100, a radiation generation unit 101 generates radiation under management by an operation management unit 107. A grid 103 is installed between an object 102 that is a target of the radiation imaging and a detection unit 104, and reduces scattered rays reaching the detection unit 104. Note, the grid 103 may be configured such that it can be removed depending on the intended use of the imaging. The detection unit 104 detects radiation which passes through the object 102 and outputs image data in accordance with the radiation. The operation management unit 107 controls synchronization between radiation generation of the radiation generation unit 101 and an imaging operation of the detection unit 104, and controls a generation condition of the radiation generation unit 101. A control unit 105 controls sensitivity of the detection unit 104 and operation settings such as frame rate based on a control setting value that a setting unit 109 set. A data collecting unit 106 collects each type of digital data included in image data outputted from the detection unit 104. An information processing unit 108 performs control of image processing and of the whole radiation imaging apparatus 100 in accordance with instructions made by a user. Each of the above described configurations are electrically connected.

The information processing unit 108 is equipped with the setting unit 109, an image processing unit 110, a CPU 115, a memory 116, a console panel 117, a storage unit 118, and a display unit 119, and these are electrically connected via a CPU bus 114. The setting unit 109 calculates, based on an imaging condition, a control setting value corresponding to a radiation detection range according to the detection unit 104. The image processing unit 110 has a preprocessing unit 111, a scattered ray reduction processing unit 112, and a diagnostic image processing unit 113. The CPU 115 realizes various control by executing programs stored in the memory 116. Note, the setting unit 109 and the image processing unit 110 may be configured by dedicated hardware, and a part or the entirety of these may be realized by the CPU 115 executing a predetermined program. Also, the control unit 105, the data collecting unit 106, and the operation management unit 107 may include the information processing unit 108, each of these parts may be configured by dedicated hardware, or may be realized by the CPU 115 executing a predetermined program. The control unit 105, the data collecting unit 106, the operation management unit 107, and the information processing unit 108 may also be independent apparatuses, and any combination of these may be realized on one apparatus. The memory 116 stores various data and the like necessary for processing by the CPU 115. Also, the memory 116 includes a work memory for work by the CPU 115. Also, the CPU 115 performs operation control and the like of the apparatus as a whole in accordance with user instructions inputted to the console panel 117.

Note, the radiation in the present specification is not limited to the typically used X-rays, and may be α-rays, β-rays, γ-rays, and the like which are beams created by particles (including photons) emitted by radioactive decay. Also, it is assumed that the radiation of the present specification may be other beams having an energy greater than or approximately equal to these, such as a particle beam or cosmic rays, for example. Below, description is given of an example in a case where X-rays are used as the radiation.

The radiation imaging apparatus 100 starts an imaging sequence for radiation imaging of the object 102 in accordance with user instructions via the console panel 117. Firstly, X-rays of a predetermined condition are irradiated from the radiation generation unit 101 and X-rays that passed through the object 102 are incident on the detection unit 104. The detection unit 104 detects the radiation (X-rays in the present embodiment), and outputs image data according to the radiation (X-ray dose, for example). The operation management unit 107 controls, in relation to the radiation generation unit 101, synchronization between voltage or current, an X-ray generation condition such as irradiation time, and operation of the detection unit 104. By this, the radiation generation unit 101 can generate X-rays of a predetermined imaging condition at an appropriate timing. The X-rays that pass through the object 102 are converted to an electrical signal by the detection unit 104 and are collected as digital image data by the data collecting unit 106. Note, the detection unit 104 operates under operation settings of a sensitivity and a framerate or the like controlled by the control unit 105.

The image data collected by the data collecting unit 106 is transferred to the information processing unit 108 via the operation management unit 107 and then is transferred and stored in the memory 116 via the CPU bus 114 in accordance with control by the CPU 115. Various image processing is applied by the image processing unit 110 to the image data stored in the memory 116. The preprocessing unit 111 performs preprocessing on the image data in order to correct characteristic variation of the detection unit 104. The scattered ray reduction processing unit 112 performs scattered ray reduction processing on the image data. The diagnostic image processing unit 113 performs preprocessing and generates an image suitable for diagnosis from the image data to which the scattered ray reduction processing was applied as necessary. The generated image is saved to the storage unit 118 and displayed by the display unit 119.

Figure 2:
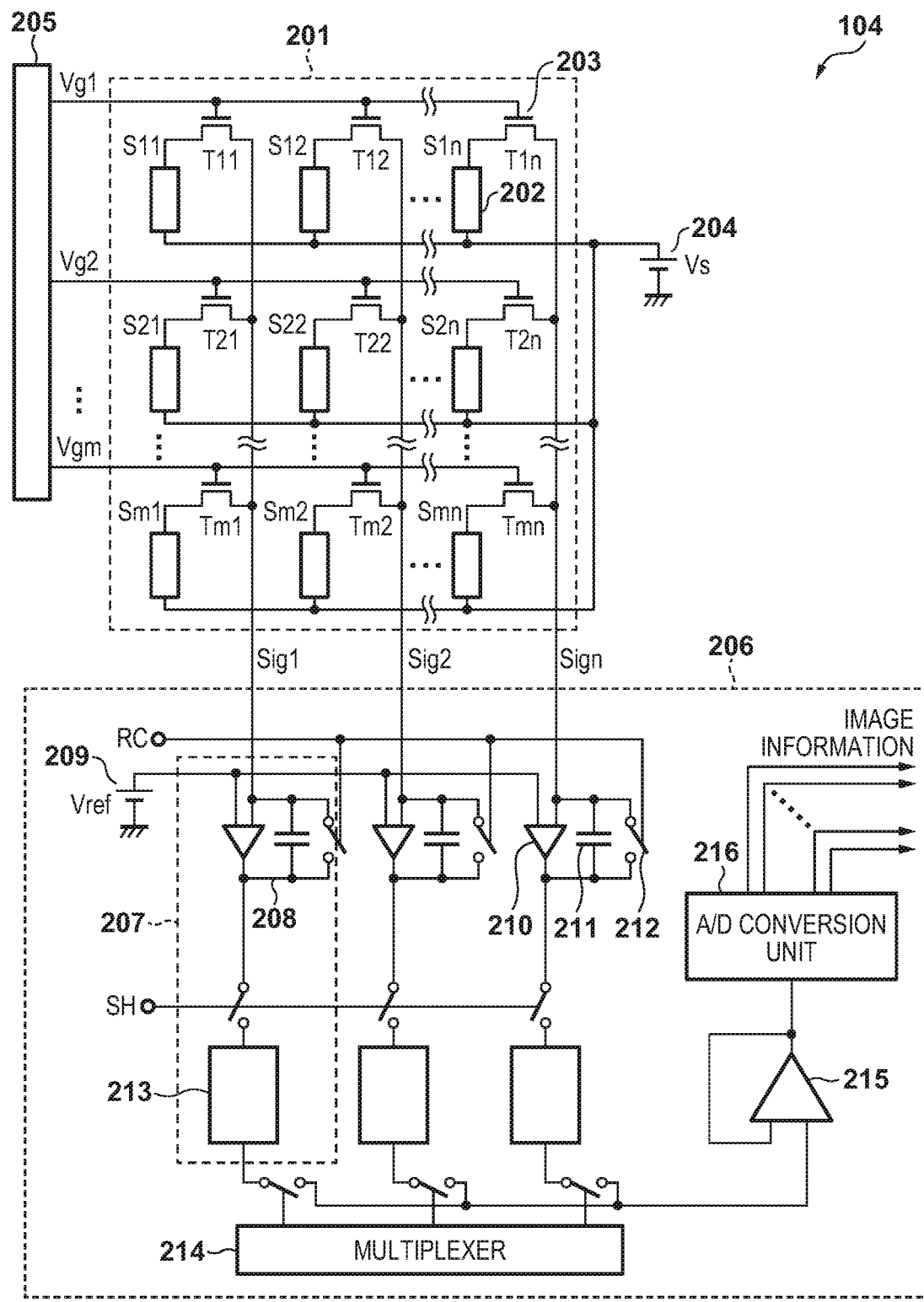
FIG. 2 is a view that illustrates a basic configuration example of a detection unit according to an embodiment.

Next, description regarding a configuration example of the detection unit 104 is given using FIG. 2. FIG. 2 is a view illustrating a configuration example of the detection unit 104 of FIG. 1. A pixel unit 201 has a plurality of pixels arranged in an array. In FIG. 2, an example in which m×n pixels are arranged two-dimensionally is schematically illustrated. Each pixel has a conversion element 202 which converts radiation to a charge and a switch element 203 which outputs an electrical signal based on the charge of the conversion element 202 in a signal line (Sig1 to Sign).

It is possible to use any pixel that has a function for converting an X-ray signal to a charge as the conversion element 202. For example, it is possible to use, as the conversion element 202, an indirect-type conversion element which combines a photoelectric conversion element for converting light to charge and a wavelength converter for converting X-rays to light of a wavelength that the photoelectric conversion element can sense. Also, it is possible to use, as the conversion element 202, a direct-type conversion element, configured by amorphous selenium, for converting X-rays to a direct charge. An example of an indirect-type conversion element which uses a PIN photodiode of mainly amorphous silicon arranged on an insulating substrate such as glass substrate as the photoelectric conversion element and uses a scintillator comprising cesium iodide (CsI) as a wavelength converter is illustrated in the present embodiment.

A transistor, such as a thin film transistor (TFT) for example, having one control terminal and two primary terminals is used as the switch element 203. One electrode of the conversion element 202 (a first electrode) is electrically connected to one of the two primary terminals of the switch element 203 and another electrode of the conversion element 202 (a second electrode) is electrically connected to a bias power source unit 204 via shared bias wiring. The bias wiring supplies a bias voltage Vs from the bias power source unit 204 to all the conversion elements 202.

The control terminals of n switch elements Tx1 to Txn of an x-th row (1≤x≤m) are electrically connected to a driving line Vgx of the x-th row, and a driving signal which controls the conductive state of the switch elements Tx1 to Txn is provided from a drive control unit 205 via the driving line Vgx. By this, the switch element is driven in units of rows. Note, the drive control unit 205 outputs, in accordance with the control signal inputted from the control unit 105, to the driving lines Vg1 to Vgm a driving signal having a conduction voltage that puts the switch elements T11 to Tmn in a conductive state and a non-conduction voltage that puts the switch elements T11 to Tmn in a non-conducting state. By this, the drive control unit 205 controls the conductive state and non-conductive state of the switch elements T11 to Tmn in units of rows, and thereby drives the pixel unit 201.

The primary terminals of a plurality of switch elements T1y to Tmy of the y-th column (1≤y≤n) not connected to the conversion element 202 are electrically connected to a signal line Sigy of the y-th column. Each of the switch elements T1y to Tmy are sequentially put into a conductive state by driving control of each line of the drive control unit 205. Electrical signals according to charge that the conversion elements S1y to Smy generate while the switch elements T1y to Tmy are sequentially put into a conductive state are sequentially outputted to a read out controller 206 via the signal line Sigy. In this way, electrical signals outputted from the plurality of pixels connected to the driving line (row) which entered a driving state according to the drive control unit 205 are outputted to the read out controller 206 in parallel via the plurality of arrayed signal lines Sig1 to Sign in the column direction. The read out controller 206 reads the signals of the plurality of the signal lines Sig1 to Sign.

In the read out controller 206, an amplification unit 207 which amplifies an electrical signal outputted in parallel from the pixel unit 201 is provided for each of the signal lines Sig1 to Sign. Each of the amplification units 207 includes an integration amplifier 208 that amplifies an electrical signal and a sample and hold unit 213 that samples and holds the electrical signal amplified by the integration amplifier 208. The integration amplifier 208 has an operational amplifier 210 which amplifies and outputs the electrical signal inputted from the signal line, a capacitor 211, and a reset switch 212. The integration amplifier 208 can change the amplification factor by changing the capacitance of the capacitor 211 (hereinafter, referred to as the integration capacitance) connected to the inverting input terminal and the output terminal of the operational amplifier 210.

The electrical signal of each of the signal lines Sig1 to Sign is inputted to an inverting input terminal of the operational amplifier 210, and a reference potential Vref generated by a reference power source unit 209 is inputted to a noninverting input terminal. An electrical signal that amplifies the difference between the reference potential Vref and the electrical signal from the signal line is outputted from the output terminal of the operational amplifier 210. The electrical signal outputted from the operational amplifier 210 is transmitted to a multiplexer 214 via the sample and hold unit 213. The multiplexer 214 sequentially outputs the electrical signals read out in parallel from each amplification unit 207. In this way, the image signals whose pixel values are aligned serially are outputted. A buffer amplifier 215 impedance-converts and outputs the image signal outputted from the multiplexer 214. The image signal which is an analog electrical signal outputted from the buffer amplifier 215 is converted to digital image data of a predetermined tonal number such as 14 bits or 16 bits for example by an A/D (analog/digital) conversion unit 216, and is outputted to the data collecting unit 106. Note, the voltages applied to the bias power source unit 204 and the reference power source unit 209 (Vs, Vref), the integration capacitance, a control setting value such as an operation clock of the drive control unit 205, and the input/output range of an A/D conversion unit 216 can be changed by the control unit 105.

Figure 3:
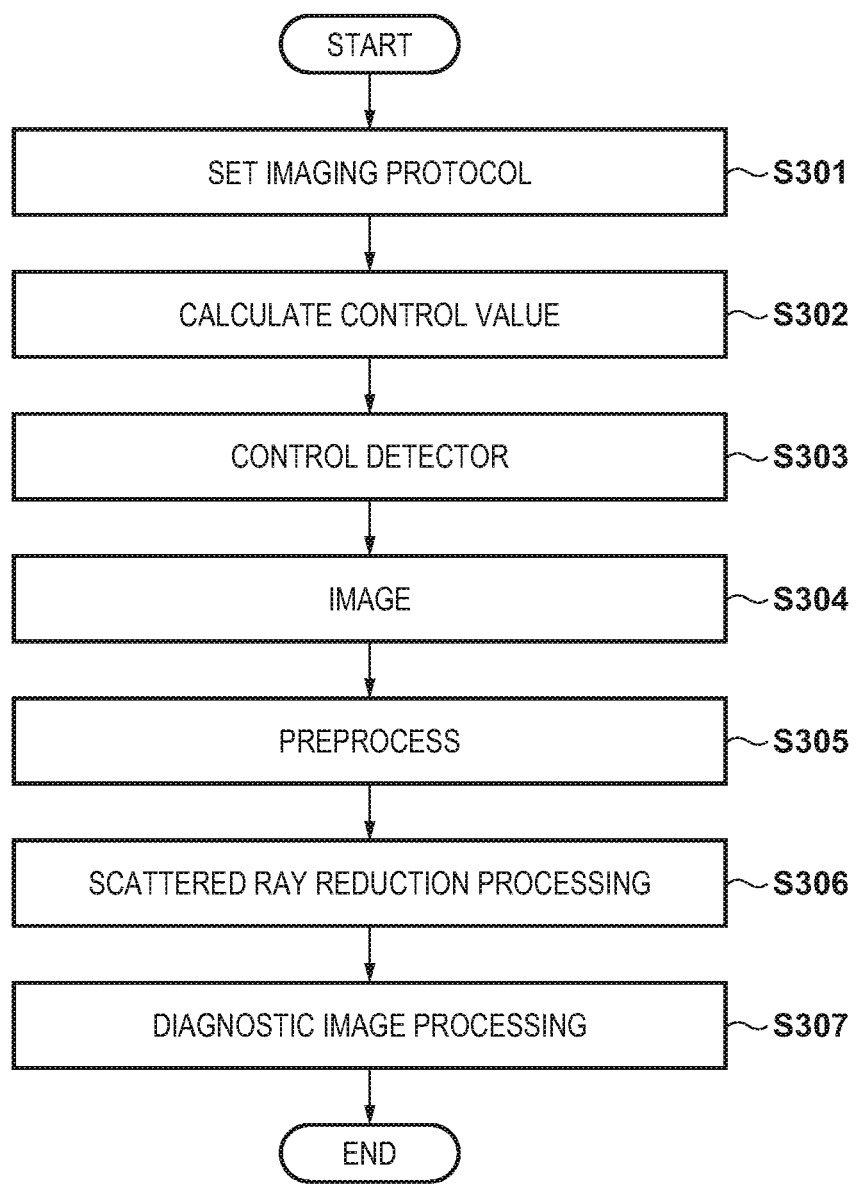
FIG. 3 is a flowchart that illustrates processing at a time of imaging in a radiation imaging apparatus according to an embodiment.

Next, description regarding processing of the control unit 105 and the setting unit 109 are given by using the flowchart of FIG. 3. FIG. 3 is a flowchart illustrating processing at a time of imaging by the radiation imaging apparatus 100.

In step S301, the CPU 115 obtains an imaging protocol that the user sets from the console panel 117, and sets each unit. The imaging protocol is a sequence of operation parameter sets of the radiation imaging apparatus 100 used when performing a desired inspection. By generating in advance an imaging protocol in which various optimum parameters are set in accordance with an imaging part or imaging method, the user can conveniently perform a condition setting according to the inspection. The imaging protocol in the present embodiment includes an imaging part of an object, an X-ray generation condition in the radiation generation unit 101 (a tube voltage and mAs value), and information of the detection unit 104 (such as an image size, pixel size, and sensitivity information). Also, the imaging protocol includes at least one of information of the presence/absence of the grid 103, information of the grid 103 (grid density and grid ratio), parameters for the preprocessing unit 111, parameters for the scattered ray reduction processing unit 112, and parameters for the diagnostic image processing unit 113. However, the above are examples of parameters associated with an imaging protocol used in a common X-ray imaging apparatus, and there is no restriction to what is described above. It is possible to use appropriate parameters in accordance with characteristics of the radiation imaging apparatus.

In step S302, the setting unit 109 performs a control value calculation process based on the imaging condition obtained by the information of the imaging protocol, and calculates a control setting value of the detection unit 104. Description regarding details of the control value calculation process of step S302 is given later. In step S303, the control unit 105 causes the control setting value calculated in step S302 to be reflected in the detection unit 104. Particularly, in step S302 to step S303, it is determined whether or not the grid 103 for scattered ray reduction is installed on the detection unit 104, and based on the determination results, the radiation detection range according to the detection unit 104 is changed. By this processing, the operation setting of the detection unit 104 is changed and an appropriate control setting value depending on whether or not a grid is used is set. By this control setting, even in a case where the input signal inputted to the detection unit 104 is increased by not using a grid for example, it is possible to set a state in the detection unit 104 in which it is difficult for saturation to occur.

In step S304, the CPU 115 causes the radiation generation unit 101 and the detection unit 104 to execute an imaging operation via the operation management unit 107. It is necessary that an imaging operation associated with X-ray generation be performed in accordance with an operation by the user. For this reason, at the stage at which the processing until step S5303 completes, the CPU 115 performs a display by the console panel 117 indicating that imaging is possible and prompts the user to make an imaging instruction. When the imaging operation of step S304 completes, the processing transitions to step S305.

In step S305, preprocessing by the preprocessing unit 111 is performed on an image obtained by the imaging operation of step S304. In the preprocessing, offset correction processing which removes a dark current of the detection unit 104, gain correction processing which corrects sensitivity fluctuations, and defect correction processing which corrects defective pixels using the surrounding pixels are performed. Offset correction processing and gain correction processing are performed by a configuration according to the control setting value of the detection unit 104 changed in step S303. For example, by obtaining a dark image for offset correction processing and an X-ray uniform irradiation image for a gain correction processing (hereinafter, correction images) subsequent to the processing of step S303 through step S304, these correction images are obtained using the control setting value used in the imaging. Also, configuration may be taken so as to obtain correction images in the plurality of control setting values in step S301 or therebefore and select and use a correction image corresponding to the current control setting value. Alternatively, configuration may be taken so as to correct a correction image obtained by using a single control setting value so as to attain an expected characteristic in accordance with the current control setting value, and then use the corrected image.

In step S306, scattered ray reduction processing by the scattered ray reduction processing unit 112 is performed. This scattered ray reduction processing is performed based on the imaging protocol set in step S301 and a result of the control value calculation process of step S302. Generally, in common X-ray imaging, it is not necessary to always perform scattered ray reduction processing because an amount of scattered rays is small in an object whose body thickness is thin, such as with imaging of a limb or an infant. The scattered ray reduction processing mainly becomes necessary for a radiation image of a trunk part such as a chest and an abdomen for which a large amount of scattered rays are generated due to a large body thickness. In other words, the scattered ray reduction processing is performed in a case where the grid 103 is not used and contrast reduction is a problem during diagnosis due to a large amount of scattered rays contained in the image. Note, regarding the details of the scattered ray reduction processing, the processing content is not restricted, and any kind of known processing may be used. For example, it is possible to use processing described in D1.

In step S307, diagnostic image processing including tone processing, enhancement processing, and noise reduction processing is performed and an image suitable for a diagnosis is generated by the diagnostic image processing unit 113. Although the diagnostic image processing is performed based on information (such as image size, pixel size, and sensitivity information) of the detection unit 104 within the imaging protocol, the control setting value of the detection unit 104 changed in step S303 is considered at that time. For example, parameters for the diagnostic image processing unit 113 within the imaging protocol are changed based on an operation setting (sensitivity of the integration amplifier 208 for example) of the detection unit 104 changed in step S303. Alternatively, configuration may be taken such that an inverse transformation for returning the sensitivity changed in step S303 to the original is performed and unchanged parameters for the diagnostic image processing unit 113 are used with respect to the image obtained in step S306.

Figure 4:
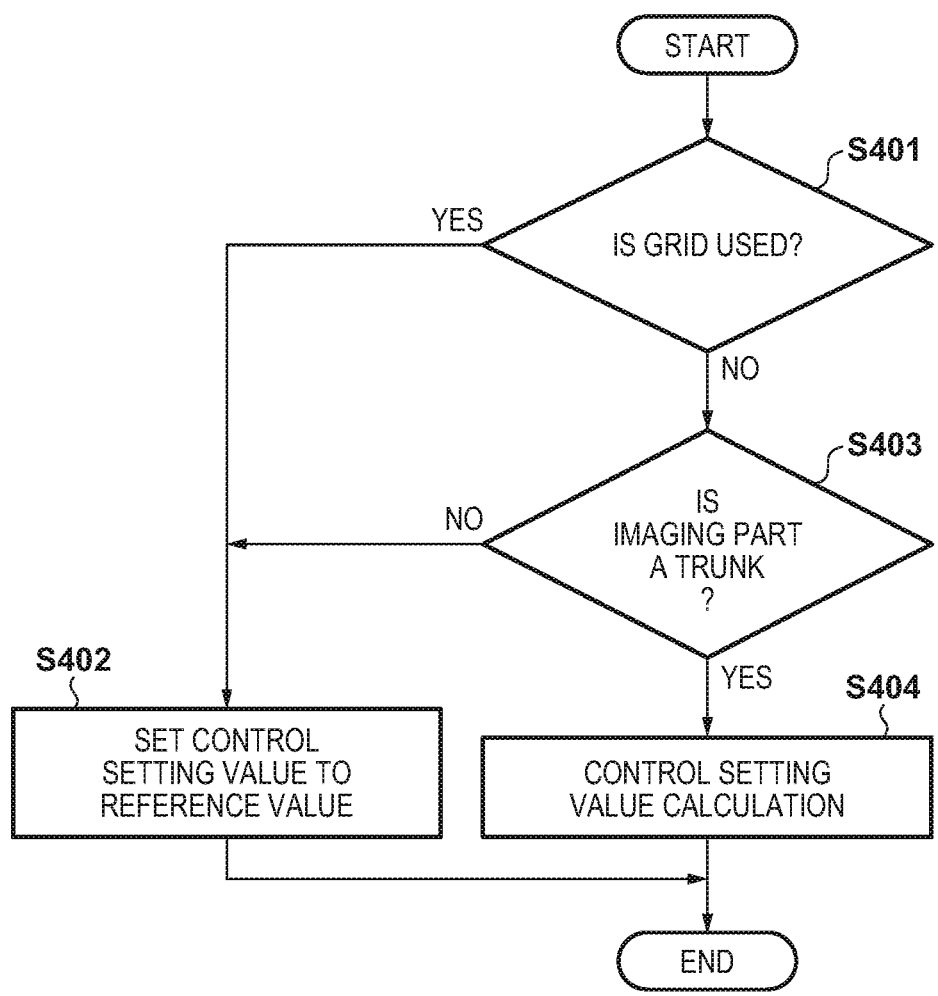
FIG. 4 is a flowchart that describes a control value calculation process of a setting unit according to the embodiment.

Next, description regarding details of the control value calculation process of the setting unit 109 in step S302 is given using FIG. 4.

By the detection unit 104 changing the control setting value, it is possible to adjust sensitivity of the output signal corresponding to the input signal (hereinafter simply referred to as sensitivity), a detection range (particularly, a maximum value of a detection range at which the signal reaches saturation (saturation dose)), an S/N ratio, and the used digital tonal number. The detection range is a dynamic range.

The history of X-ray radiography is long thus the imaging conditions for when a grid is used have been more or less optimized. Generally, the control setting value of the detection unit 104 is set such that best characteristics are obtained when the grid 103 is used. Accordingly, in the present embodiment, description regarding a method of setting the control setting value in a case where a grid is not used is given where the optimized control setting value for when the grid 103 is used is made to be the reference (reference setting).

As described above, the setting unit 109 determines whether or not the grid 103 for scattered ray reduction is installed on the detection unit 104, and based on the determination results, changes the radiation detection range according to the detection unit 104. In other words, the setting unit 109 changes the dynamic range of the detection unit 104 based on the determination result. However, in order to prevent the detection range of the detection unit 104 from being changed unnecessarily, the setting unit 109 of the present embodiment, in a case where the grid 103 is determined to not be installed, further decides whether or not to perform a change of the detection range based on the imaging part. Hereinafter, a more detailed description is given with reference to FIG. 4.

In step S401, the setting unit 109 determines whether or not the grid 103 is used. Whether or not the grid 103 is used can be determined from information within the imaging protocol. Also, configuration may be taken such that a unit for storing the detection unit 104 and the grid are electrically connected, information of the presence or absence of the grid is collected by the data collecting unit 106, and it is determined whether or not the grid 103 is used based on the results for example. In a case where it is determined that the grid is being used in step S401, imaging is performed in a state in which a possibility of an excessive signal being inputted to the detection unit 104 is low because scattered rays from the input signal of the detection unit 104 will be removed. Accordingly, in step S402, the setting unit 109 employs the above described reference setting for the control setting value. In other words, the control setting value remains at the reference setting (reference value), and is not changed.

The processing advances to step S403 in a case where it is determined that the grid 103 is not used in step S401. In step S403, the setting unit 109 obtains the build and imaging part of the object from the information within the imaging protocol. The setting unit 109 determines that a possibility of saturation occurring in the detection unit 104 is low in cases such as when the imaging part is a limb and when the object is an infant. Accordingly, the setting unit 109 advances the processing to step S402 and keeps the control setting value at the reference value. Meanwhile, in step S403, in a case where a trunk part such as a chest and abdomen having a large body thickness is the imaging part, the setting unit 109 determines that a possibility that the detection unit 104 will be saturated is high because many irradiated X-rays and also many scattered rays may be generated. In such a case, the setting unit 109 calculates the control setting value for increasing the saturation dose of the detection unit 104 in step S404. The control setting value calculated by the setting unit 109 is set to the detection unit 104 via the operation management unit 107 and the control unit 105. In this way, the detection range of the radiation according to the detection unit 104 is changed. Note, configuration may be such that step S404 is executed irrespective of the imaging part in a case where it is determined that the grid 103 is not used in step S401.

Next, description regarding a method of changing the detection range in the detection unit 104 by the setting unit 109 is given. The setting unit 109 sets the detection range to a first range in a case where it is determined that the grid 103 is installed (reference setting in the present embodiment), and sets the detection range to a second range different from the first range in a case where it is determined that the grid 103 is not installed. Here, a saturation dose which is the upper limit of the second range is higher than a saturation dose which is the upper limit of the first range.

As described above, the detection unit 104 includes pixels (the pixel unit 201) that convert the radiation to an electrical signal, the integration amplifier 208 that amplifies the electrical signal, and the A/D conversion unit 216 that AD-converts the output of the integration amplifier 208, and

[Method A] Changing the amplification factor of the integration amplifier 208,

[Method B] Changing the input/output range of the A/D conversion unit 216,

[Method C] Changing the saturation dose in the pixel, and the like can be considered as methods of changing the detection range for example.

Saturation of the detection unit 104 can be broadly divided into two types: that which is generated by the input/output range of the A/D conversion unit 216 being exceeded in the read out controller 206 and that which is generated by the detection range of the radiation of the conversion element 202 within the pixel unit 201 being exceeded. In a case of the former where saturation originating in the read out controller 206 is generated, it is possible to apply a change of the detection range by method A or method B. In a case of the latter where saturation originating in the conversion element 202 is generated, it is possible to apply a change of the detection range by method C.

Firstly, description regarding a change of the detection range by method A is given. In a case according to method A, the setting unit 109 adjusts the sensitivity and the saturation dose of the integration amplifier 208 of the detection unit 104 by changing the integration capacitance (the capacitance of the capacitor 211) for example. In other words, the setting unit 109 changes the integration capacitance to cause the sensitivity (amplification factor) of the detection unit 104 to decrease, and enters a state in which the saturation dose is increased as a result. In such a case, the control setting value is represented by a value of the integration capacitance (capacitance of the capacitor 211) in the amplification unit 207. Hereinafter, description regarding the method of setting the integration capacitance is given.

Firstly, the target sensitivity of the integration amplifier 208 is set to a sensitivity at which it can be guaranteed that a saturation dose will be of a level that does not cause clinical problems even if imaging is performed without using a grid. A method in which the amount of scattered rays from a primary X-ray transmittance of the grid used in imaging an imaging part is estimated is described as an example of the method of calculating the target sensitivity. If the primary X-ray transmittance of the grid assumed to be used in the imaging part obtained in step S403 is Xp and the sensitivity when the integration capacitance is the reference setting is Sstd, the target sensitivity St can be calculated from St=Sstd×Xp. By this, without using a grid, it is possible to set so that even when the scattered rays are added to the input signal of the detection unit 104, the saturation dose increases in proportion to the addition of scattered rays. Alternatively, configuration may be taken such that a coefficient p is set for each imaging part and/or X-ray generation condition (tube voltage/mAs value) and stored as correspondence information. In such a case, the coefficient p corresponding to the imaging part and X-ray generation conditions designated in the imaging protocol is selected from the correspondence information and the target sensitivity St (=Sstd×p) is set by multiplying the coefficient p with the sensitivity Sstd of the reference setting. The coefficient p is a value having a sufficient margin for the scattered rays that may be added to the input signal, such as 0.5 for example.

Figures 5A, 5B:
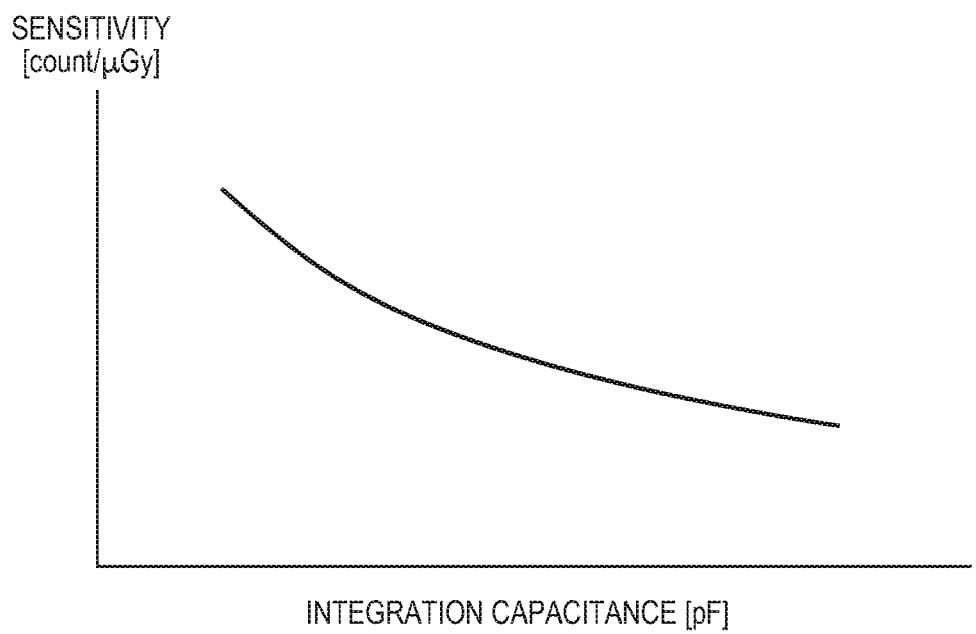
FIG. 5A is a diagram that illustrates an example of a relationship between integration capacitance, a sensitivity of the detection unit, and a saturation dose.
FIG. 5B is a diagram that illustrates an example of a relationship between integration capacitance and a sensitivity of the detection unit.

Next, the integration capacitance for realizing the target sensitivity is calculated. FIG. 5A is a diagram that illustrates an example of a relationship between integration capacitance, a sensitivity of the detection unit 104, and a saturation dose. When an integration capacitance is cf and a constant unique to the detection unit 104 is A, a sensitivity S is inversely proportional to the integration capacitance cf and the sensitivity S is represented by $S=A\times(1/cf)$ as in FIG. 5B. A case is considered in which the target sensitivity St is a signal of 800 counts per 1 microGray (represented as 800[count/µGy]), the sensitivity Sstd of the reference setting is 1200[count/gGy], and the integration capacitance of this case is 2 [pF]. In such a case, the integration capacitance for achieving the target sensitivity St=800[count/µGy] is calculated as 3 [pF] according to the relationship of the above described sensitivity and integration capacitance. By this, it becomes possible to increase the saturation dose (55 µGy to 80 µGy).

Note, depending on the implementation of the integration amplifier 208, configuration may be taken such that the integration capacitance can be set to discrete values, and in such a case, the closest integration capacitance that is larger than the foregoing calculated cf may be selected.

Figure 6:
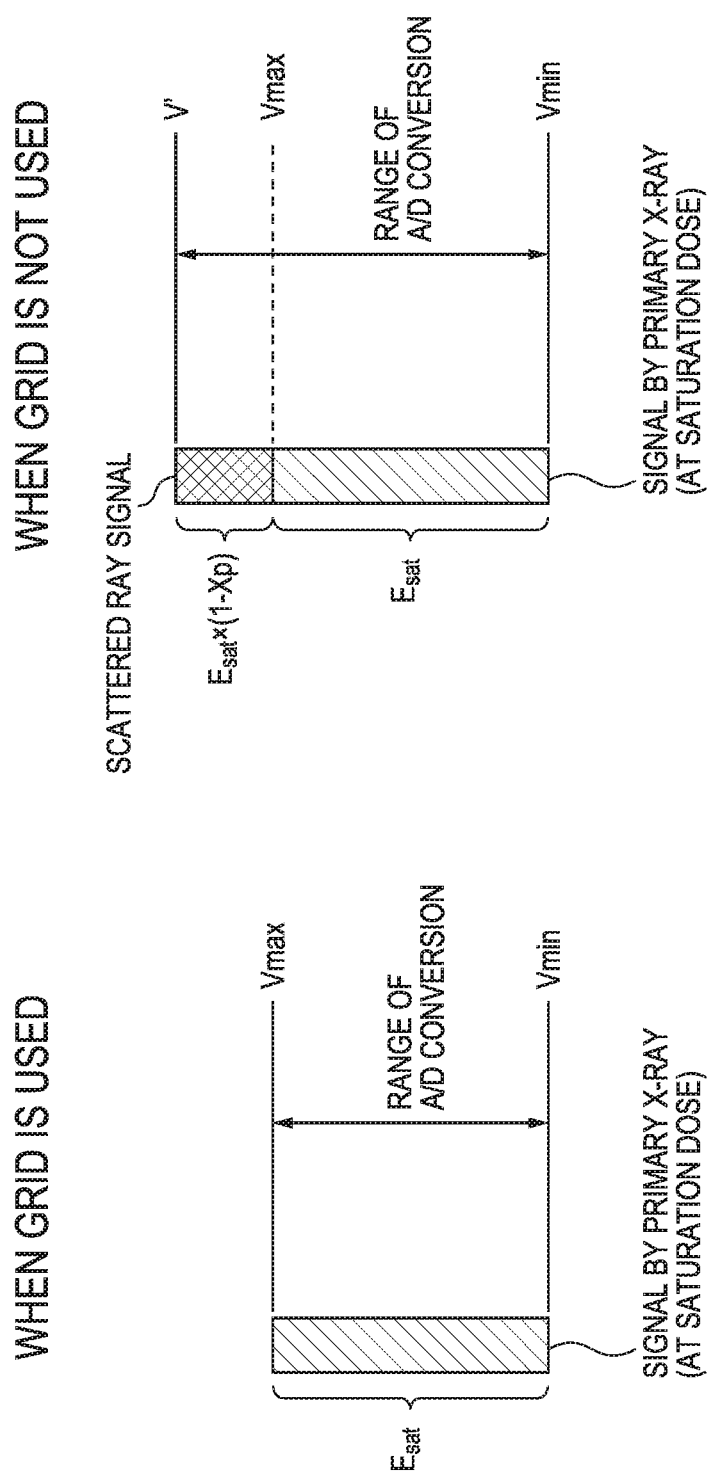
FIG. 6 is a diagram that illustrates a relationship between a signal that is inputted to the detection unit and an input/output range of an A/D conversion unit.

Thereafter, description regarding an embodiment (method A) in which a saturation dose is increased by changing the integration capacitance constant in the amplification unit 207. Next, method B (an embodiment in which the input/output range of the A/D conversion unit 216 is changed without causing the amplification factor of the amplification unit 207 to change) is described as another embodiment. As illustrated in FIG. 6, the input/output range of the A/D conversion unit 216 in the reference setting is Vmin to Vmax, the input/output range of a case where a grid is not used is Vmin to V', and the saturation dose at a time of the reference setting is Esat. Also, a case is considered in which the A/D conversion unit 216 performs a linear digital value conversion on a potential difference inputted within the input/output range. In a case where the grid is not used, since a signal E that can be inputted to the detection unit 104 is estimated to be $E=Esat+Esat\times(1-Xp)$, $V=Vmax+(Vmax-Vmin)\times(1-Xp)$, for example, is set.

Note, configuration may be taken such that even in method B, similarly to method A, a predetermined constant is set separately for each imaging part and/or X-ray generation condition (tube voltage/the mAs value), and stored as correspondence information. In such a case, a constant corresponding to the imaging part and the X-ray generation condition designated in the imaging protocol is obtained from the correspondence information and the input/output range is set by adding the constant to Vmax.

Description regarding a change of the detection range by method C is given as another embodiment of step S404. Method C is processing effective in cases where saturation of the detection unit 104 is generated by the radiation exceeding the detection range in the conversion element 202 of the pixel unit 201.

The bias voltage Vs set by the bias power source unit 204 and the reference voltage Vref set by the reference power source unit 209 are applied to the conversion element 202. Generally, the saturation dose of the conversion element 202 is in a proportional relationship to the potential difference between Vs and Vref, and the saturation dose becomes larger the greater (Vs−Vref) becomes. For example, Vref is fixed to a predetermined value, and when a saturation dose is made to be E, a proportionality constant defined by the characteristics of the conversion element 202 is made to be B, and an offset constant is made to be C, it is possible to adjust the saturation dose by a relationship of $E=B\times Vs+C$ by changing Vs. In accordance with this, when the saturation dose at a time of the reference setting is made to be Esat and the bias voltage is made to be Vsstd, a bias voltage V' of a case where the grid is not used may be set as $V'=Esat\times(1-Xp)/B+Vsstd$.

Note, configuration may be taken such that even in method C, similarly to methods A and B, a predetermined constant is set separately for each imaging part and/or X-ray generation condition (tube voltage/the mAs value), and stored as correspondence information. In such a case, a constant corresponding to the imaging part and the X-ray generation condition designated in the imaging protocol is obtained from the correspondence information and Vs and/or Vref is changed based on this.

Thereafter, although methods A to C are described as methods of changing the detection range of the radiation in the detection unit 104, the methods of changing the detection range are not limited to these. Also, although a control setting value when the grid 103 is installed is made to be the reference above, it is clear that a control setting value when the grid 103 is not installed may also be the reference. In short, it is possible to make the detection range of radiation appropriately different when the grid 103 is installed and when the grid 103 is not installed. Also, in the foregoing, although it is determined whether or not the detection range of the detection unit 104 changes based on the presence or absence of a grid or based on the presence or absence of the grid and on the imaging part, configuration may be taken such that the detection range of the detection unit 104 is changed in accordance with whether or not the scattered ray reduction processing is executed. The scattered ray reduction processing is processing executed in a case where there is no grid, and configuration may be taken such that it is determined whether or not the scattered ray reduction processing is executed instead of determining whether or not a grid is used in step S401 of FIG. 4, for example. Also, configuration may be taken such that processing is advanced to step S402 in a case where it is determined that the scattered ray reduction processing is not executed, and processing is advanced to step S403 in a case where it is determined that the scattered ray reduction processing is executed.

Also, it is illustrated in the above described methods A to C that the detectable range of the radiation is changed based on the primary radiation transmittance (the primary X-ray transmittance Xp) of the grid 103. By this, control of the detection range suitable to the characteristics of the grid that is attached/detached is realized. Also, in methods A to C, correspondence information indicating correspondence between a parameter for deciding the detection range and an imaging part is held, and a detection range is changed based on the parameter associated with the designated imaging part. By changing the detection range using such correspondence information, it is possible to adjust the detection range with the generated amount corresponding to different scattered rays for each imaging part.

As described above, by virtue of the present embodiment, in a case where a signal of scattered rays is added to an input signal, it is possible to increase the signal amount of the scattered rays and the saturation dose and to set a suitable signal detection range. As a result, it becomes possible to provide a radiation imaging apparatus that can obtain a high contrast object image while preventing image destruction from occurring due to saturation of the detection unit, even when imaging without using a grid.

Embodiment(s) of the present invention can also be realized by a computer of a system or apparatus that reads out and executes computer executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-108322, filed May 31, 2017, which is hereby incorporated by reference herein in its entirety.

What is claimed is:

1. A radiation imaging apparatus, comprising:
a detection unit configured to detect radiation and output image data;
a determination unit configured to determine whether or not a grid for scattered ray reduction is installed on the detection unit; and
a change unit configured to, based on a determination result of the determination unit, change a radiation detection range of the detection unit.

2. The apparatus according to claim 1, wherein the detection range is a dynamic range of the detection unit, and the change unit changes the dynamic range of the detection unit based on the determination result of the determination unit.

3. The apparatus according to claim 1, wherein the change unit sets the detection range to a first range in a case where it is determined that the grid is installed, and sets the detection range to a second range different to the first range in a case where it is determined that the grid is not installed.

4. The apparatus according to claim 3, wherein a saturation dose which is an upper limit of the second range is higher than a saturation dose which is an upper limit of the first range.

5. The apparatus according to claim 1, wherein the change unit, in a case where it is determined that the grid is not installed, further decides whether or not to change the detection range based on an imaging part.

6. The apparatus according to claim 1, further comprising an execution unit configured to, in a case where it is determined by the determination unit that the grid is not installed, execute scattered ray reduction processing.

7. The apparatus according to claim 1, wherein the detection unit includes a pixel configured to convert radiation into an electrical signal, an integration amplifier configured to amplify the electrical signal, and an A/D conversion unit configured to perform an A/D conversion of output of the integration amplifier, and
the change unit changes an amplification factor of the integration amplifier.

8. The apparatus according to claim 7, wherein the change unit changes a capacitance of a capacitor configured to control the amplification factor of the integration amplifier.

9. The apparatus according to claim 7, wherein the change unit, in a case where it is determined that the grid is not installed, lowers a sensitivity of the integration amplifier.

10. The apparatus according to claim 1, wherein the detection unit includes a pixel configured to convert radiation into an electrical signal, an integration amplifier configured to amplify the electrical signal, and an A/D conversion unit configured to perform an A/D conversion of output of the integration amplifier, and
the change unit changes an input/output range of the A/D conversion unit.

11. The apparatus according to claim 1, wherein the detection unit includes a pixel configured to convert radiation into an electrical signal, an integration amplifier configured to amplify the electrical signal, and an A/D conversion unit configured to perform an A/D conversion of output of the integration amplifier, and
the change unit changes a saturation dose in the pixel.

12. The apparatus according to claim 11, wherein the change unit changes a voltage of a difference between a bias voltage applied to the pixel and a reference voltage of the integration amplifier.

13. The apparatus according to claim 1, wherein the change unit changes the detection range based on primary radiation transmittance of the grid.

14. The apparatus according to claim 1, further comprising a holding unit configured to hold correspondence information indicating correspondence between an imaging part and a parameter for deciding the detection range, wherein
the change unit changes the detection range based on a parameter associated with a designated imaging part.

15. A radiation imaging apparatus, comprising:
a detection unit configured to detect radiation and output image data according to the detected radiation;
a determination unit configured to determine whether or not to execute scattered ray reduction processing for the image data; and
a change unit configured to, based on whether or not to execute the scattered ray reduction processing, change a radiation detection range of the detection unit.

16. A radiation imaging method for detecting radiation and outputting image data according to the detected radiation, the method comprising:
determining whether or not a grid for scattered ray reduction is installed; and
changing a radiation detection range based on a result of the determination.

17. A radiation imaging method for detecting radiation and outputting image data according to the detected radiation, the method comprising:
determining whether or not to execute scattered ray reduction processing for the image data; and
based on whether or not to execute the scattered ray reduction processing, changing a radiation detection range.

18. A non-transitory storage medium storing a program for causing a computer to execute a radiation imaging method for detecting radiation and outputting image data according to the detected radiation, the method comprising:
determining whether or not a grid for scattered ray reduction is installed; and
changing a radiation detection range based on a result of the determination.

19. A non-transitory storage medium storing a program for causing a computer to execute a radiation imaging method for detecting radiation and outputting image data according to the detected radiation, the method comprising:

determining whether or not to execute scattered ray reduction processing for the image data; and based on whether or not to execute the scattered ray reduction processing, changing a radiation detection range.

* * * * *